(12) United States Patent
Heath et al.

(10) Patent No.: US 10,660,580 B2
(45) Date of Patent: May 26, 2020

(54) DIRECTED X-RAY FIELDS FOR TOMOSYNTHESIS

(71) Applicant: Carestream Health, Inc., Rochester, NY (US)

(72) Inventors: Michael D. Heath, Rochester, NY (US); Xiaohui Wang, Pittsford, NY (US); David H. Foos, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 119 days.

(21) Appl. No.: 14/647,544

(22) PCT Filed: Jan. 22, 2014

(86) PCT No.: PCT/US2014/012493
§ 371 (c)(1),
(2) Date: May 27, 2015

(87) PCT Pub. No.: WO2014/116665
PCT Pub. Date: Jul. 31, 2014

(65) Prior Publication Data
US 2015/0320371 A1   Nov. 12, 2015

Related U.S. Application Data

(60) Provisional application No. 61/755,488, filed on Jan. 23, 2013.

(51) Int. Cl.
*H05G 1/54* (2006.01)
*A61B 6/02* (2006.01)
(Continued)

(52) U.S. Cl.
CPC .............. *A61B 6/025* (2013.01); *A61B 6/06* (2013.01); *A61B 6/4007* (2013.01);
(Continued)

(58) Field of Classification Search
None
See application file for complete search history.

(56) References Cited

U.S. PATENT DOCUMENTS

| 8,452,379 B2 * | 5/2013 | DeFreitas | A61B 6/502 |
| | | | 600/427 |
| 8,712,138 B2 * | 4/2014 | Gleich | A61B 6/4241 |
| | | | 382/132 |

(Continued)

FOREIGN PATENT DOCUMENTS

| CN | 101466313 A | * | 6/2009 | ............. A61B 6/466 |
| CN | 101466313 A | | 6/2009 | |

(Continued)

OTHER PUBLICATIONS

Partial International Search Report dated Jul. 22, 2012 for International Application No. PCT/US2014/012493, 3 pages.

(Continued)

*Primary Examiner* — Andrew Smyth

(57) ABSTRACT

Radiographic imaging systems and/or methods embodiments capable of both tomosynthesis x-ray imaging and general projection radiography x-ray imaging can include a single x-ray source assembly including a plurality of distributed x-ray sources, where at least one of the plurality of distributed x-ray sources is configured to output a beam sufficient for standard projection radiography, and each of at least two of the plurality of distributed x-ray sources is configured to output a beam at a lower radiation dose sufficient for tomosynthesis. In one embodiment, radiographic imaging systems and/or methods embodiments can include a single x-ray source; a first collimator that is configured to be adjustable for at least two dimensions; and a second collimator that is configured to provide fixed (Continued)

collimation. In one embodiment, a single x-ray source can include a single radiation shield or a single vacuum chamber.

16 Claims, 14 Drawing Sheets

(51) Int. Cl.
  *A61B 6/00* (2006.01)
  *G21K 1/04* (2006.01)
  *A61B 6/06* (2006.01)
(52) U.S. Cl.
  CPC ............ *A61B 6/5205* (2013.01); *A61B 6/542* (2013.01); *G21K 1/04* (2013.01)

(56) References Cited

U.S. PATENT DOCUMENTS

| | | | | |
|---|---|---|---|---|
| 2005/0135664 A1* | 6/2005 | Kaufhold | ............ | G06T 11/006 382/131 |
| 2006/0268409 A1* | 11/2006 | Tan | ............ | A61B 6/06 359/485.07 |
| 2007/0140419 A1* | 6/2007 | Souchay | ............ | A61B 6/466 378/37 |
| 2008/0095420 A1* | 4/2008 | Ohyu | ............ | A61B 6/025 382/131 |
| 2008/0267484 A1* | 10/2008 | Chen | ............ | A61B 6/032 382/132 |
| 2008/0317212 A1* | 12/2008 | Kuehn | ............ | A61B 6/06 378/151 |
| 2009/0323893 A1* | 12/2009 | Hanke | ............ | A61B 6/502 378/37 |
| 2010/0091940 A1* | 4/2010 | Ludwig | ............ | A61B 6/025 378/22 |
| 2010/0290593 A1* | 11/2010 | Legagneux | ............ | H01J 35/065 378/122 |
| 2011/0122992 A1* | 5/2011 | Hanke | ............ | H01J 35/10 378/37 |
| 2012/0183197 A1* | 7/2012 | Gleich | ............ | A61B 6/4241 382/132 |
| 2012/0195403 A1* | 8/2012 | Vedantham | ............ | A61B 6/022 378/4 |
| 2013/0272494 A1* | 10/2013 | DeFreitas | ............ | A61B 6/025 378/37 |

FOREIGN PATENT DOCUMENTS

| | | | | | |
|---|---|---|---|---|---|
| CN | 101951837 A | | 1/2011 | | |
| CN | 101951837 A | * | 1/2011 | ............ | A61B 6/4007 |
| CN | 101466313 B | * | 11/2012 | ............ | H05G 1/70 |
| CN | 101951837 B | * | 2/2013 | ............ | A61B 6/4007 |
| DE | 10 2010 062 541 A1 | | 6/2012 | | |
| DE | 102010062541 A1 | * | 6/2012 | ............ | A61B 6/025 |
| DE | 102010062541 A1 | * | 6/2012 | ............ | A61B 6/542 |
| JP | 50-060969 U | | 6/1975 | | |
| JP | S58-45542 A | | 3/1983 | | |
| JP | 2005-261838 | | 9/2005 | | |
| JP | 2005296647 A | * | 10/2005 | ............ | A61B 6/025 |
| JP | 2005296647 A | * | 10/2005 | ............ | A61B 6/4007 |
| JP | 2010-110498 | | 5/2010 | | |
| JP | 2011-512004 | | 4/2011 | | |
| WO | WO 2007/120744 A2 | | 10/2007 | | |
| WO | WO-2007120744 A2 | * | 10/2007 | ............ | G21K 1/025 |
| WO | WO 2007/120744 A2 | * | 10/2007 | ............ | A61B 6/025 |
| WO | WO 2007/120744 A3 | * | 6/2008 | ............ | A61B 6/025 |
| WO | WO-2007120744 A3 | * | 6/2008 | ............ | A61B 6/4028 |
| WO | 2011/153555 | | 12/2011 | | |
| WO | WO-2011153555 A2 | * | 12/2011 | ............ | A61B 6/4078 |
| WO | WO-2011153555 A3 | * | 1/2012 | ............ | A61B 6/0414 |
| WO | WO 2013/126502 A1 | | 8/2013 | | |
| WO | WO-2013126502 A1 | * | 8/2013 | ............ | A61B 6/4405 |
| WO | WO 2013126502 A1 | * | 8/2013 | ............ | A61B 6/03 |

OTHER PUBLICATIONS

International Search Report dated Dec. 11, 2014 for International Application No. PCT/US2014/012493, 3 pages.
J. Zhang et al., entitled "Stationary scanning x-ray source based on carbon nanotube field emitters," Applied Physics Letter, 86, 2005, pp. 184104-1-184104-3.
Chinese Search Report, dated Jun. 1, 2017, for Chinese Application No. 201480003888.2, 3 pages.

* cited by examiner

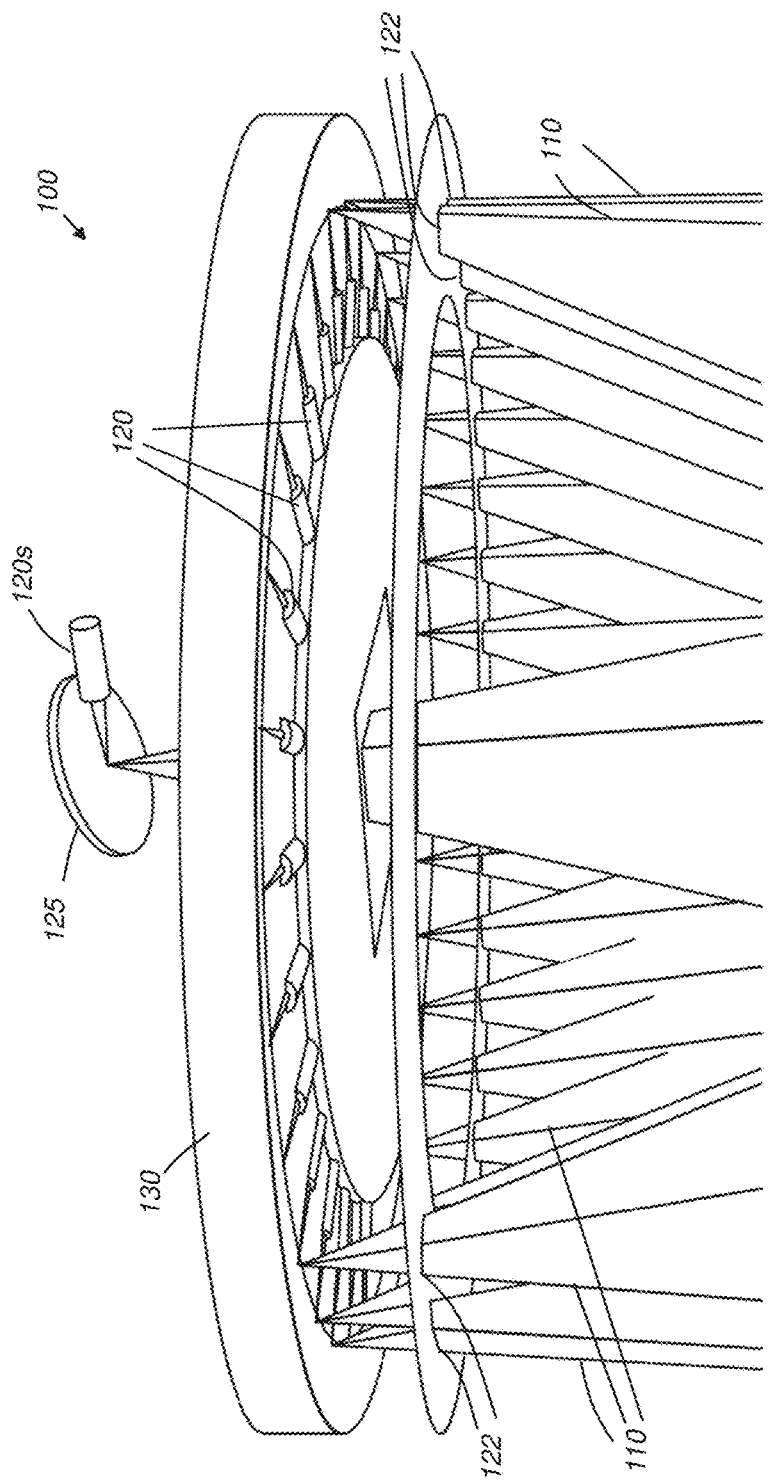

DIRECTED X-RAY FIELDS FOR TOMOSYNTHESIS

CROSS REFERENCE TO RELATED APPLICATIONS

This application claims the benefit of and is a U.S. National Phase filing of PCT Application PCT/US14/12493 filed Jan. 22, 2014 entitled "DIRECTED X-RAY FIELDS FOR TOMOSYNTHESIS", in the name of Michael D. Heath, et al, which claims the benefit of U.S. Provisional application U.S. Ser. No. 61/755,488, filed on Jan. 23, 2013, entitled "DIRECTED X-RAY FIELDS FOR TOMOSYNTHESIS", in the names of Michael D. Heath, et al., which is incorporated herein by reference in its entirety.

FIELD OF THE INVENTION

The invention relates generally to the field of medical imaging, and in particular to radiographic imaging apparatus. More specifically, the invention relates to a radiographic imaging systems and/or methods including tomosynthesis imaging.

BACKGROUND

Digital X-ray tomosynthesis is an imaging technique that enables three-dimensional imaging of a patient using a large-area digital detector typically used for conventional (single projection) radiography. A finite number of projection images over a limited angular range, typically between 20° and 40°, are acquired by varying the orientations of the x-ray tube, patient and detector. This is usually accomplished by either moving both the detector and x-ray source or by fixing the position of the detector (source) and moving the x-ray source (detector). In applications where the detector is fixed, multiple spatially distributed X-ray sources may be used or movable sources may be displaced in various patterns or trajectories. Three-dimensional data is reconstructed from the captured projections in the form of a number of slices through the patient anatomy, each parallel to the detector plane. A consequence of limited angular scanning is that the in depth resolution is much lower than the in-plane resolution of the reconstructed object.

SUMMARY OF THE INVENTION

An aspect of this application is to advance the art of radiography tomosynthesis systems.

Another aspect of this application to address in whole or in part, at least the foregoing and other deficiencies in the related art.

It is another aspect of this application to provide in whole or in part, at least the advantages described herein.

Another aspect of the application is to provide methods and/or apparatus by which radiographic imaging systems and/or methods can include tomosynthesis imaging.

Another aspect of the application is to provide imaging methods and/or apparatus embodiments by which a radiation source assembly can acquire projections images to generate the reconstruction of two-dimensional and three-dimensional tomosynthesis images.

Another aspect of the application is to provide imaging methods and/or apparatus embodiments by which a single x-ray source assembly can include a plurality of distributed x-ray sources, where at least one of the plurality of distributed x-ray sources to output a beam for standard projection radiography, and each of at least two of the plurality of distributed x-ray sources output a beam for tomosynthesis. In one embodiment, single x-ray source assembly can be enclosed in single vacuum or radiation shield.

Another aspect of the application is to provide imaging methods and/or apparatus embodiments by which a single x-ray source assembly can include a plurality of distributed x-ray sources, where groups of distributed x-ray sources for tomosynthesis are independently adjustable such as for different focal lengths, SIDs or dimensions.

Another aspect of the application is to provide imaging methods and/or apparatus embodiments by which a single x-ray source assembly can include a plurality of distributed x-ray sources to operate in both a first projection radiography mode and a tomosynthesis mode with independent collimation for both modes. In one embodiment, collimation for the tomosynthesis mode include as plurality of beam shapes and/or source positions.

Another aspect of the application is to provide imaging methods and/or apparatus embodiments by which a single x-ray source assembly can include a plurality of distributed x-ray sources to operate in a tomosynthesis mode with anode sharing for two or more of the distributed x-ray sources.

In accordance with one embodiment, the present invention can provide a method for digital radiographic 3D tomographic image reconstruction, executed at least in part on a computer, that can include operating a single x-ray source assembly including a plurality of distributed x-ray sources in a first mode for standard projection radiography, and operating the single x-ray source assembly in a second mode for tomosynthesis. In one embodiment, the single x-ray source assembly can be enclosed in single vacuum or radiation shield. In one embodiment, the method can include independently adjusting collimation in the second mode.

In accordance with one embodiment, the present invention can provide a radiographic imaging system capable of both tomosynthesis x-ray imaging and general projection radiography x-ray imaging, the radiographic imaging system that can include a single x-ray source assembly including a plurality of distributed x-ray sources, where at least one of the plurality of distributed x-ray sources is configured to output a beam sufficient for standard projection radiography, and each of at least two of the plurality of distributed x-ray sources is configured to output a beam at a lower radiation dose sufficient for tomosynthesis; an x-ray generator; and a control unit to control each x-ray source.

In accordance with one embodiment, the present invention can provide a radiographic imaging system capable of both tomosynthesis x-ray imaging and projection x-ray imaging, the radiographic imaging system that can include a single x-ray source; a first collimator that is configured to be adjustable for at least two dimensions; and a second collimator that is configured to provide fixed collimation.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of exemplary embodiments of the invention, as illustrated in the accompanying drawings.

The elements of the drawings are not necessarily to scale relative to each other.

FIGS. 1A-1H is a diagram that shows a perspective view of a portion of a radiation source assembly for general and tomography radiographic imaging systems and/or methods that can implement both projection and tomographic imaging according to embodiments of the application.

FIG. 4 shows the 3-Dimensional nature of the directed x-ray fields.

DESCRIPTION OF EXEMPLARY EMBODIMENTS

Figure 1A:
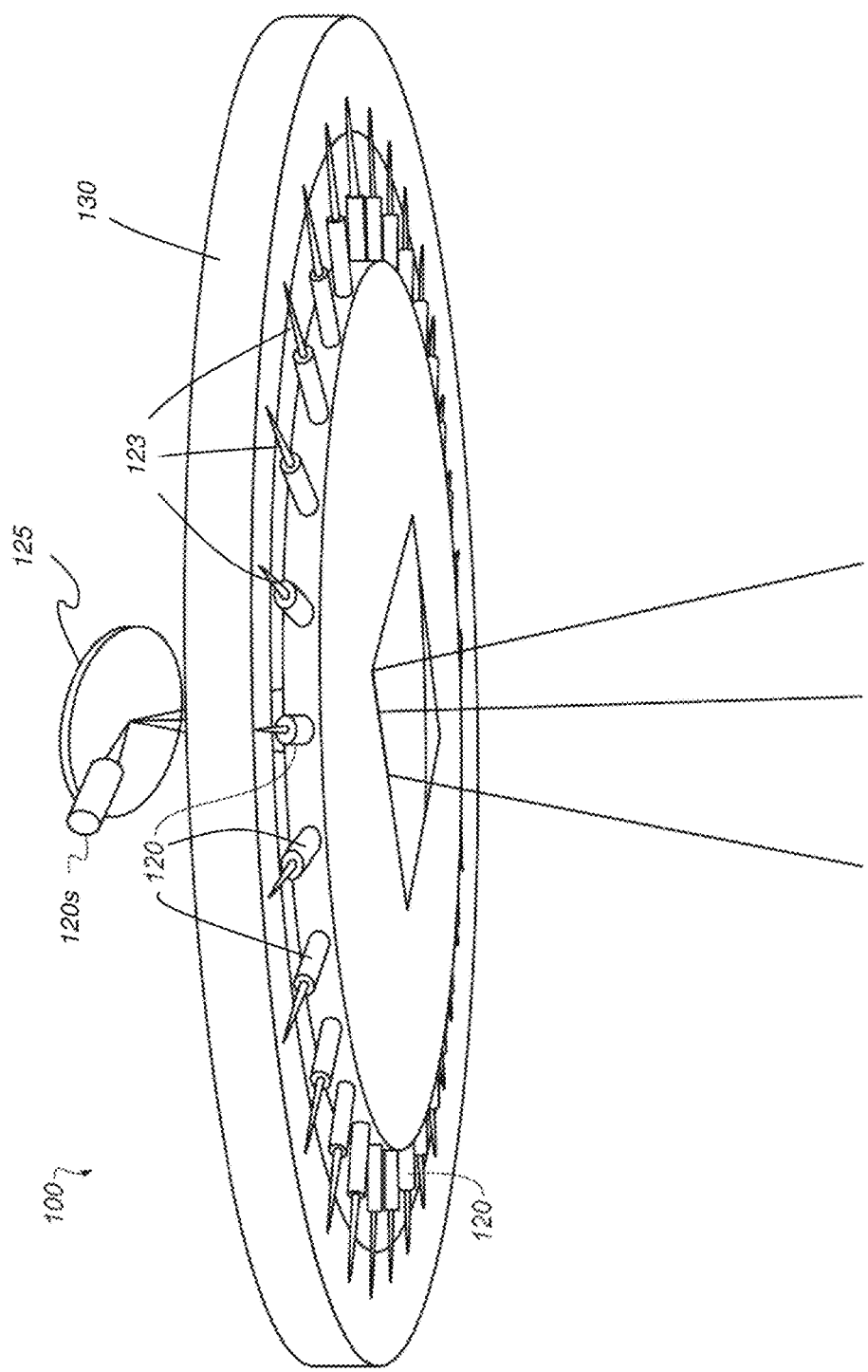
Figure 1B:
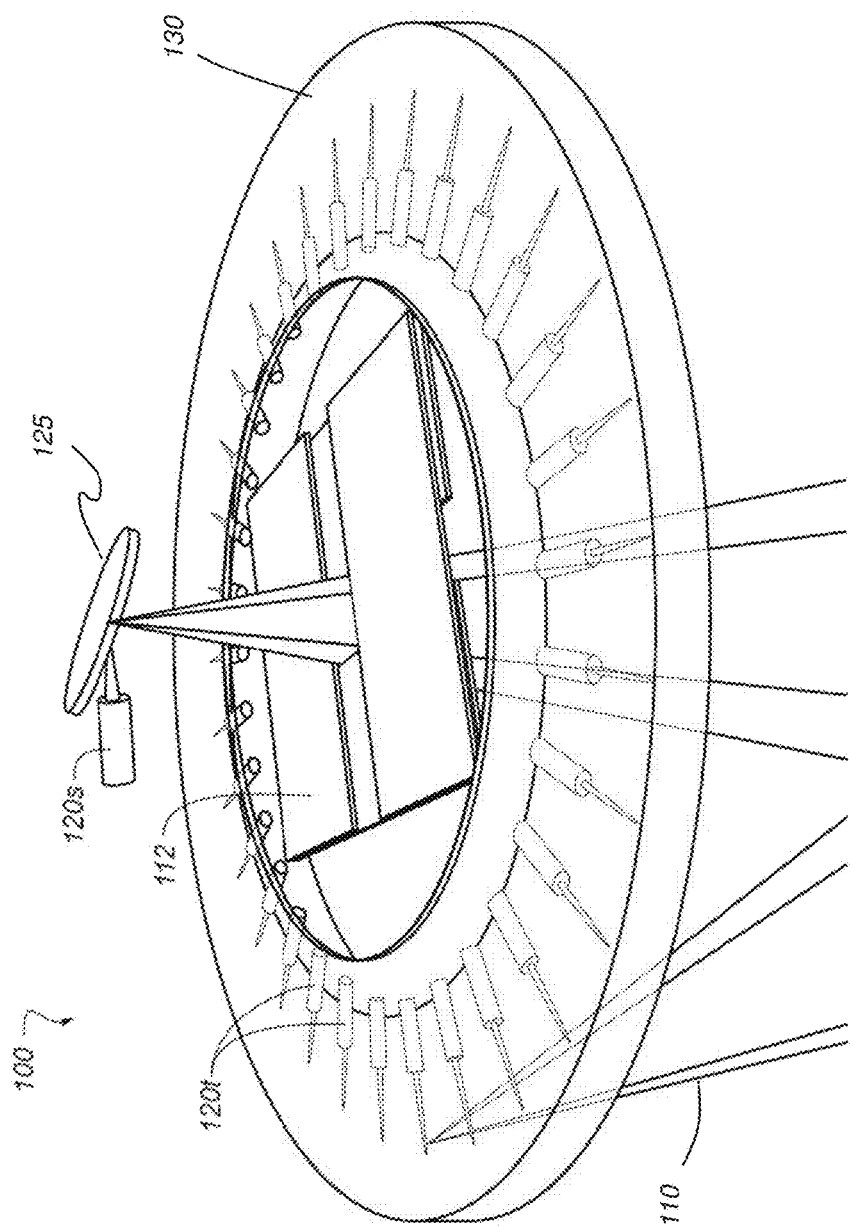
Figure 1C:
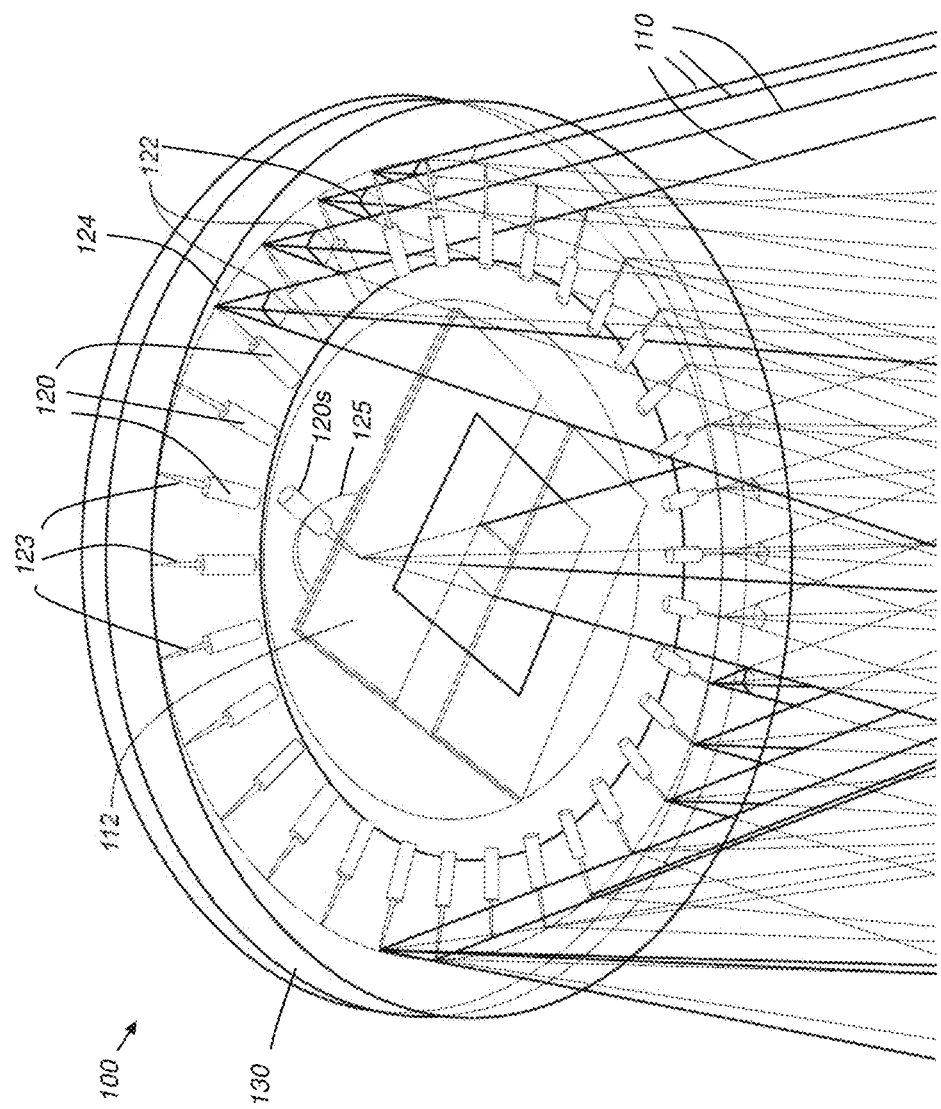
Figure 1D:
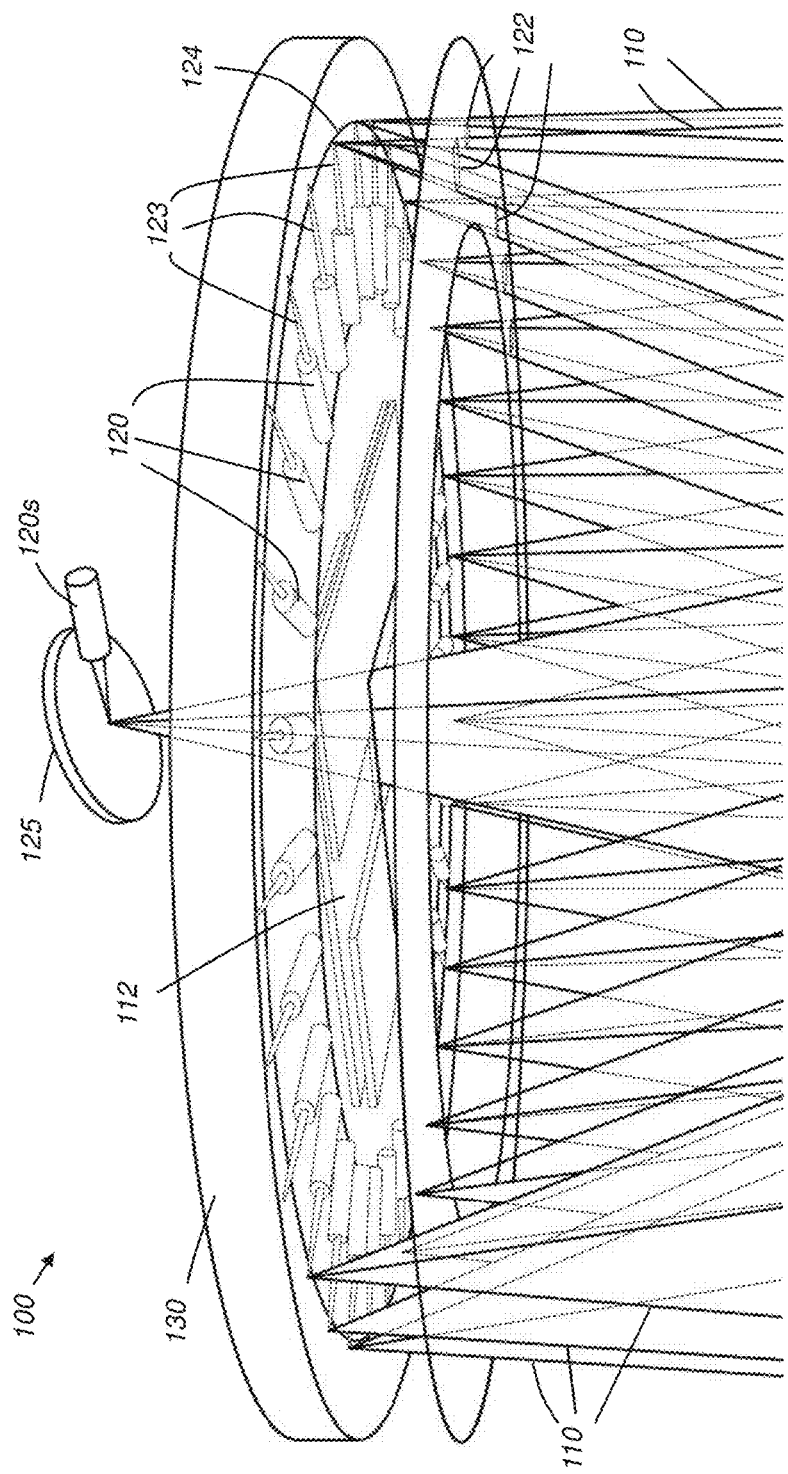
Figure 1E:
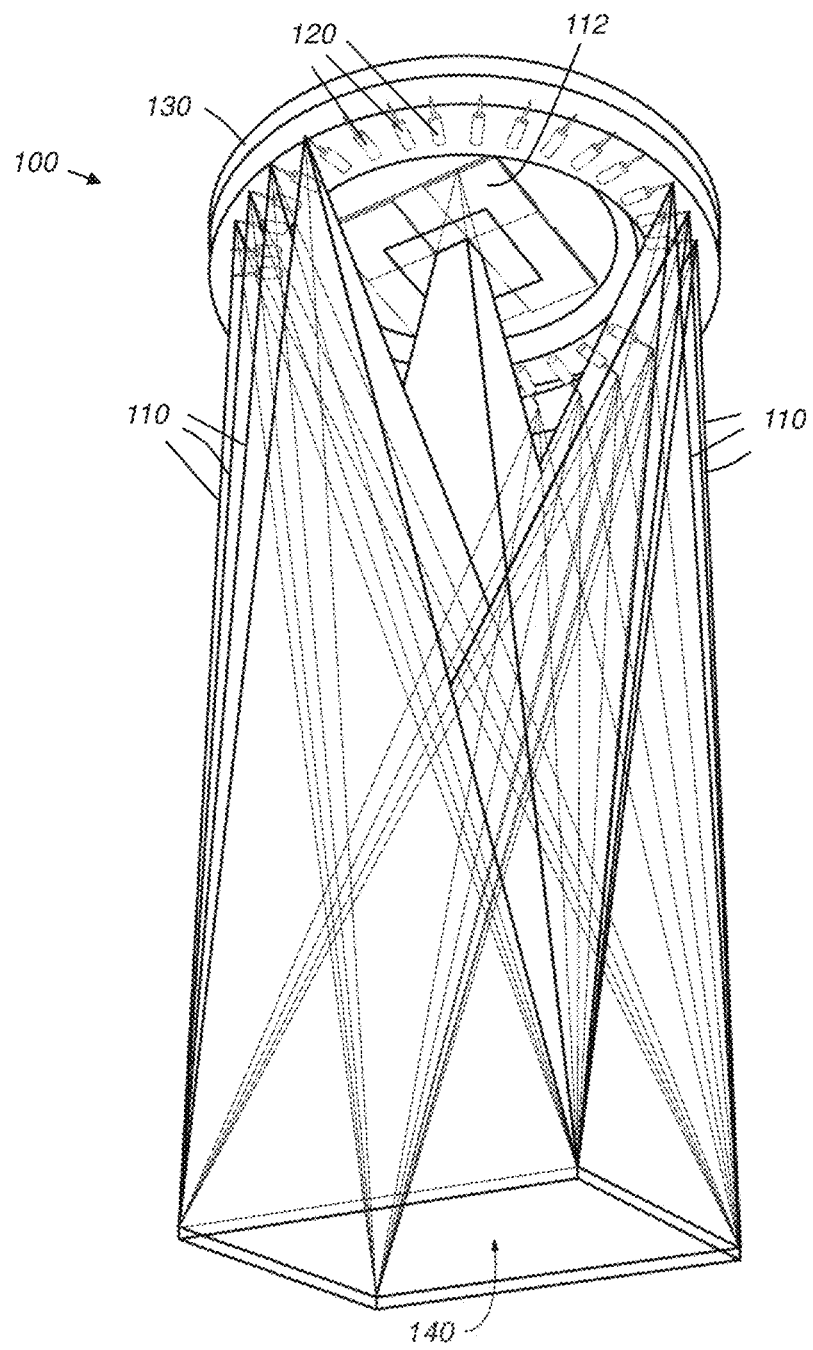
Figure 1F:
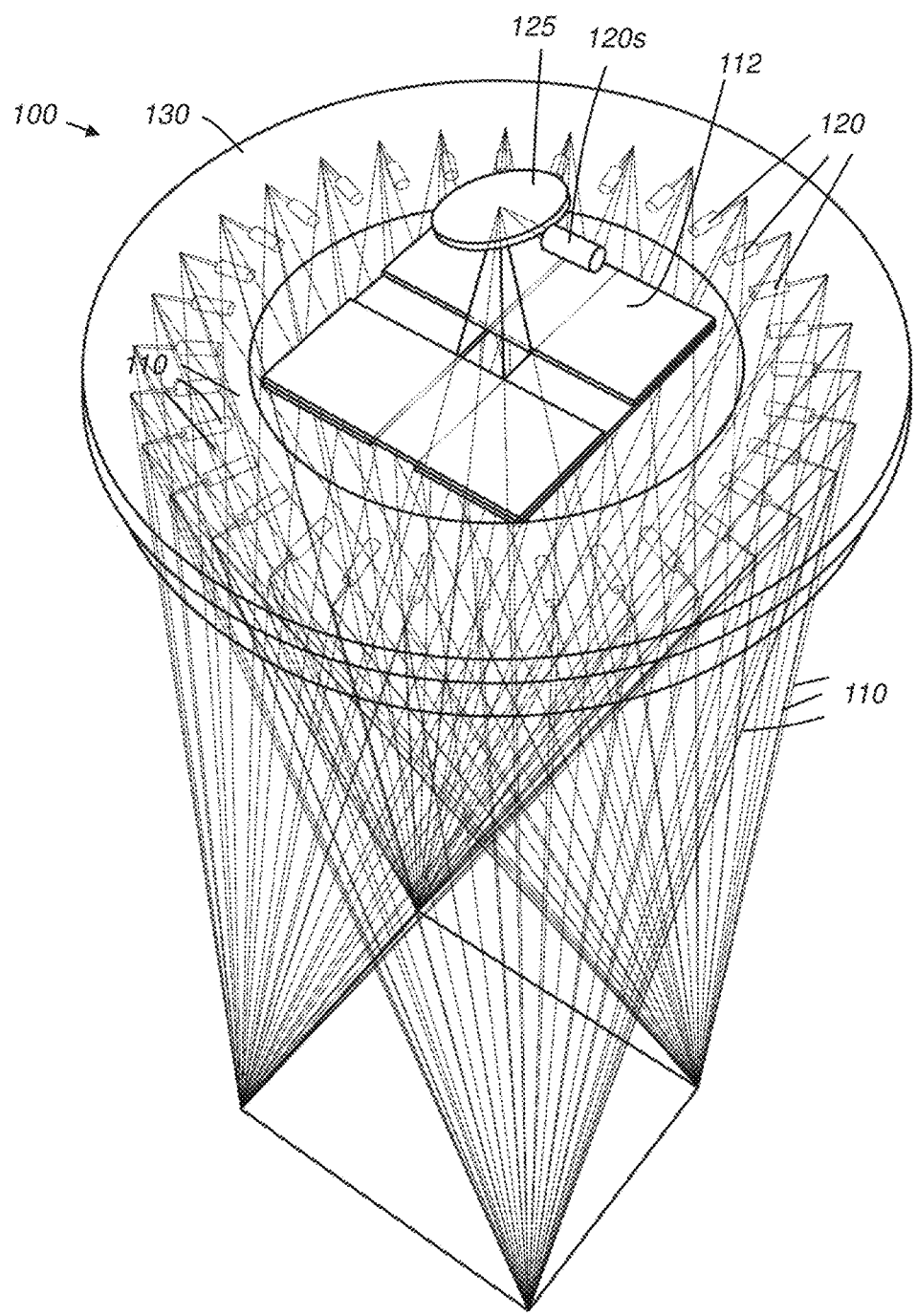
Figure 1G:
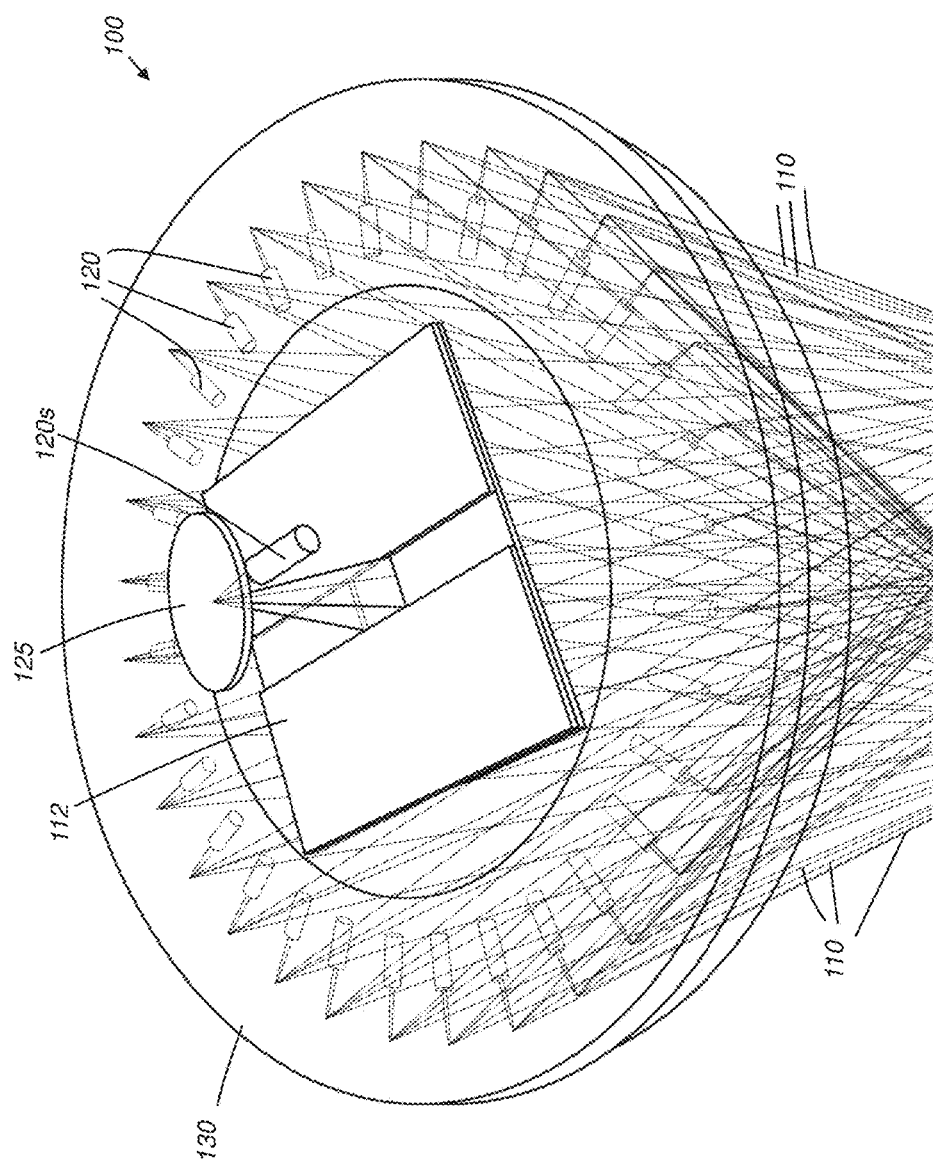

The following is a description of exemplary embodiments according to the invention, reference being made to the drawings in which the same reference numerals identify the same elements of structure in each of the several figures. Where they are used, the terms "first", "second", and so on, do not necessarily denote any ordinal or priority relation, but may be used for more clearly distinguishing one element or time interval from another.

Portable radiographic systems are routinely used in hospitals. Compared to standard projection radiography, tomosynthesis provides improved depiction of fine details not visible in normal radiographs due to overlying structures. These benefits provide the impetus to develop portable tomosynthesis systems that can be utilized in the intensive care unit, emergency department, and operating rooms where moving patient is either impracticable or ill advised due to the risk of doing further damage to the patient.

Exemplary system and/or method embodiments according to the application can address various problems in tomosynthesis imaging. First, embodiments can provide exemplary ways to perform both traditional radiographic projection imaging and tomosynthesis with distributed sources using one radiographic imaging system. Second, embodiments can provide exemplary selectable collimation fields for the distributed sources, independent of collimation of the central x-ray source used for more traditional projection x-ray imaging. Third, embodiments can provide exemplary ways to reduce anode heating at locations (e.g., at points) of the anode where the focal spots of the distributed x-ray sources impact the anode.

Exemplary embodiments can address various problems by arranging the x-ray sources in a prescribed shape such as a circle, and providing a movable or rotatable collimator that simultaneously collimates a plurality of sources or all of the sources while allowing the selection of one or more collimation fields. Exemplary embodiments can provide various capture geometries for the plurality of distributed sources and/or a central standard radiographic projection x-ray source. In certain exemplary embodiments, an array of distributed sources can include at least one x-ray source capable of standard radiographic projection x-ray imaging. Certain exemplary embodiments can provide a shared anode for the distributed sources that can further be movable or rotatable to reduce potential damage to the anode at the x-ray focal spots.

Figure 2:
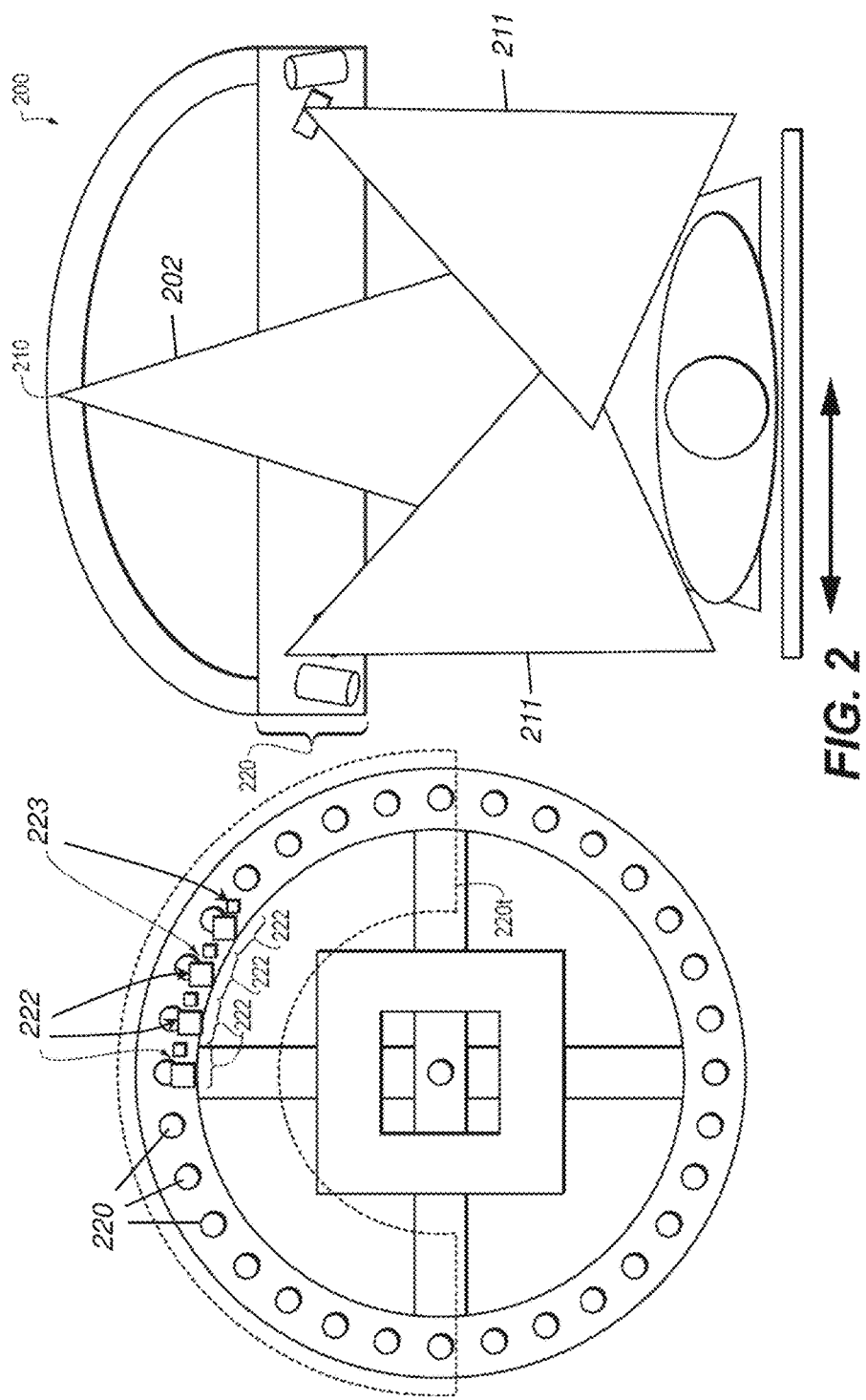
FIG. 2 is a diagram that shows a perspective view of a radiation source assembly for general and tomography radiographic imaging systems and/or methods that can implement at least two collimations for a plurality of beams for at least tomographic imaging and projection imaging according to embodiments of the application.
Figure 3:
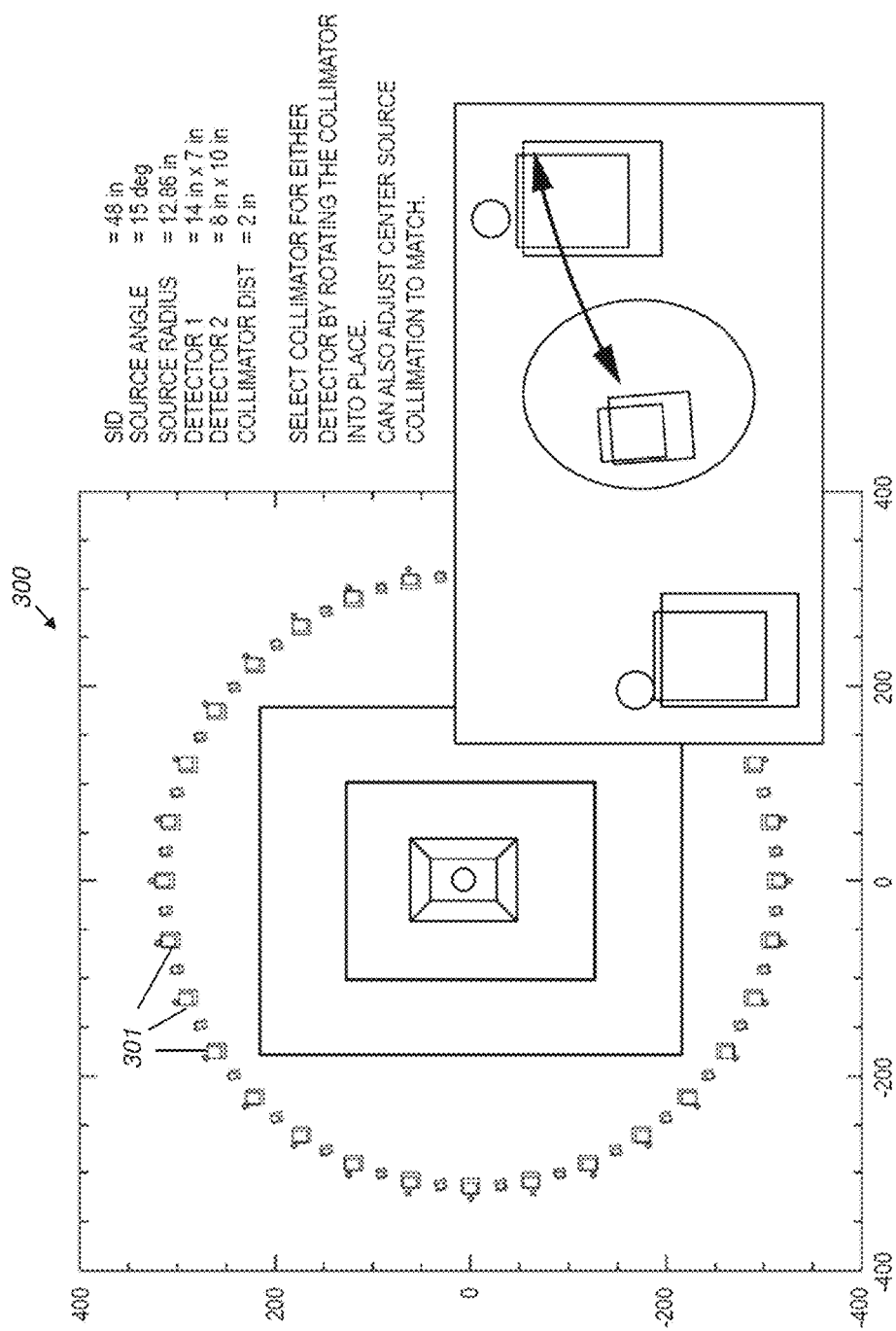
FIG. 3 is a diagram that shows use of selectable collimators for each source in an exemplary radiation source assembly embodiment with at least two selectable positions for selectable collimation according to the application.
Figure 4:
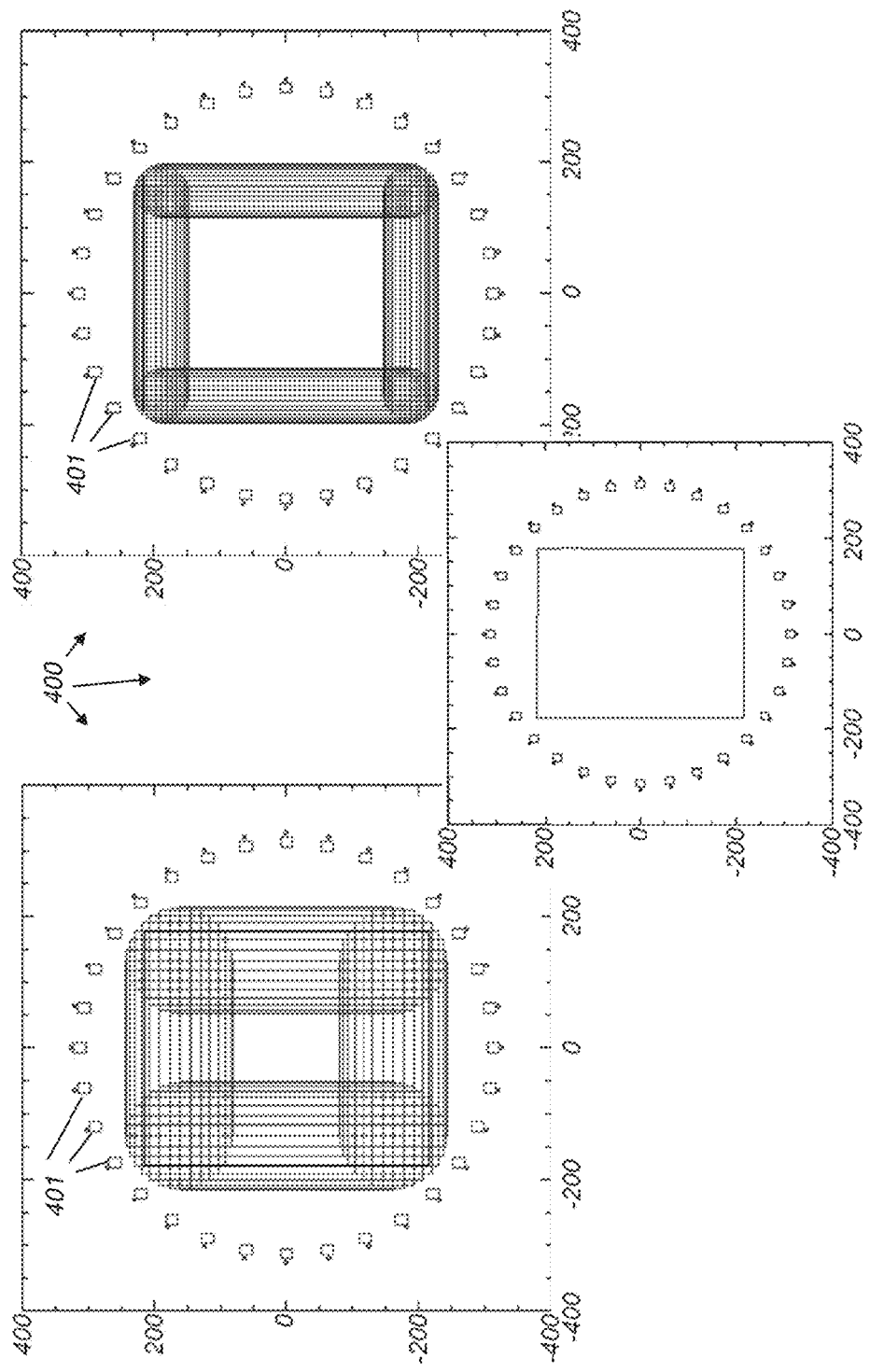
FIG. 4 is a diagram that shows exemplary intersections of collimated x-ray fields with planes at three different preset heights (12, 6, and 0 inches) from a detector according to the application.
Figure 5:
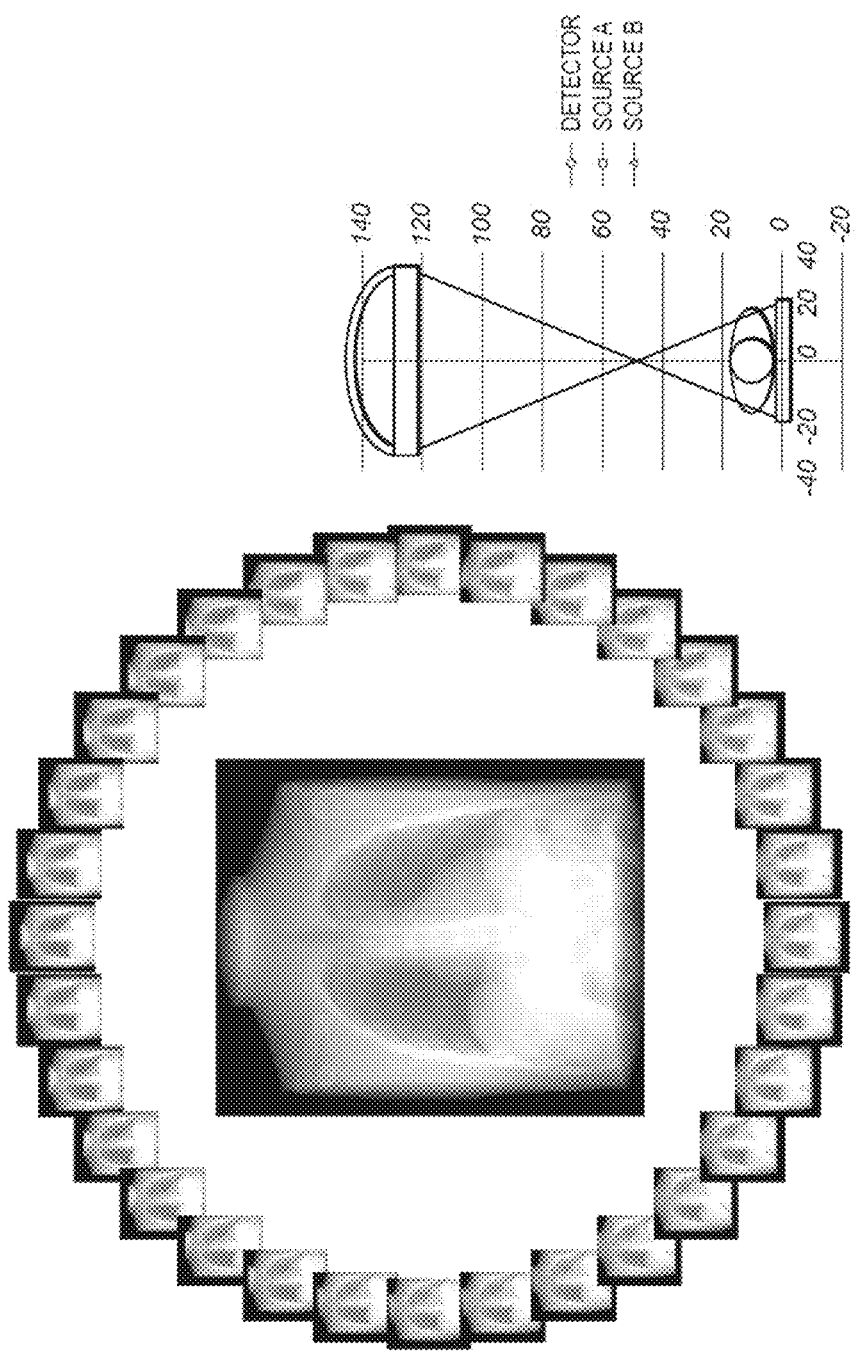
FIG. 5 is a diagram that shows simulations of exemplary projection x-ray images from each source position according to another embodiment of the application.
Figure 6:
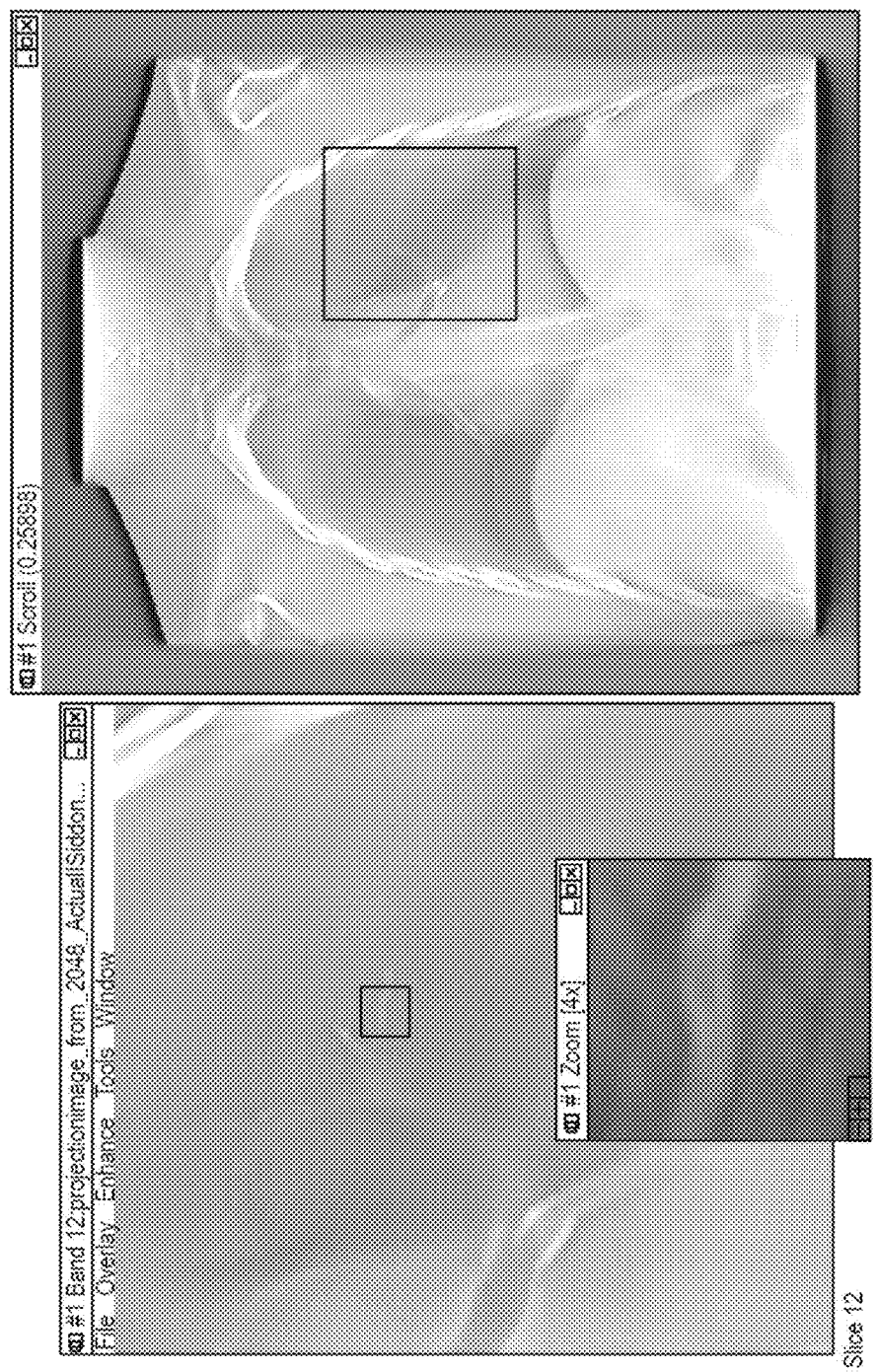
FIG. 6 is a diagram that shows a simulation of an exemplary reconstruction from about 30 projection x-ray images (±20 deg) that can provide a tomosynthesis capability according to embodiments of the application.

FIGS. 1A-1H shows perspective views of a design arrangement of a portion of a radiation source assembly 100 for radiographic imaging systems according one exemplary embodiment. As shown in FIGS. 1A-1H, a radiation source assembly 100 for radiographic imaging systems and/or methods can implement both projection and tomographic imaging according to embodiments of the application. FIGS. 2-4 illustrate exemplary ring structures 200, 300, 400, that each also has an exemplary collimator 222, 301, 401, capable of at least two positions. For certain embodiments, in one position a collimator 222, 301, 401, can collimate the x-ray fields 211 of a plurality of or all arranged sources (e.g., low power distributed sources or tomosynthesis sources) to one region and in another position the collimator can collimate the fields of all sources to a different region. FIG. 2 is a diagram that shows an embodiment of a selectable collimator. FIG. 3 is a diagram that shows two selectable positions (e.g., of 3D shaped collimation units) rotated into place for selectable collimator embodiment. FIG. 4 is a diagram that shows the intersection of the collimated fields with planes at different heights (e.g., from a detector). FIG. 4 shows the 3-Dimensional nature of the directed x-ray fields. FIG. 5 is a diagram that shows simulations of exemplary projection x-rays from each source position. FIG. 6 is a diagram that shows simulation of an exemplary reconstruction from the exemplary projection x-rays.

As shown in FIGS. 1A-1H, a radiation source assembly 100 for radiographic imaging systems and/or methods can implement both projection and tomographic imaging according to embodiments of the application. The radiation source assembly 100 can include an array of distributed sources 120 (e.g., CNT x-ray sources) having a prescribed shape where at least one of the distributed sources 120s can output a beam sufficient for standard projection radiography. The radiation source assembly 100 can include a tomosynthesis imaging source that can be a subset 120t of the array of distributed sources 120 that can have a prescribed shape. The radiation source assembly 100 can output x-ray beams 110 to impinge a digital radiographic detector 140. In one embodiment, a collimator 112 for the distributed source 120s can be fully adjustable. In one embodiment, one or more collimators 122 for the distributed source 120t can be selectively adjustable between two or more positions. In one exemplary embodiment, the radiation source assembly 100 can include a shared anode 130 for the distributed sources 120t that can further be rotated around in a circular manner to reduce potential damage to the shared anode 130 at the x-ray focal spots.

FIG. 2 is a diagram that shows an exemplary ring structure for a radiation source assembly 200 for radiographic imaging systems and/or methods that can implement both projection and tomographic imaging, and that also has an exemplary collimator 222 capable of at least two positions. As shown in FIG. 2, a radiation source assembly 200 can include an array of distributed sources 220 (e.g., CNT x-ray sources) having a prescribed shape and at least one source 210 for standard projection radiography. The radiation source assembly 200 can include a tomosynthesis imaging source that can be a subset 220t of the array of distributed sources 220 that can have a prescribed shape. As shown in FIG. 2, in one position one or more collimators 222 can collimate the x-ray fields 211 of the subset 220t of distributed sources to one region and in another position the collimator 222 can collimate the fields 211 of the subset 220t of distributed sources to a different region. FIG. 2 is a diagram that shows an exemplary embodiment of a first selectable collimator 222 and a second selectable collimator 223.

In one embodiment, the arranged or distributed low power sources 120, 220 can be an array of carbon-nanotube x-ray sources. In one embodiment, a plurality or all of the electron beams 123 emitted by the carbon nanotube sources arranged in the circle, are directed at a single, shared anode 130. This anode embodiment can be a disc with a hole in the center. For example, one anode embodiment can have a beveled edge 124 so the electron beam 113 can impinge the anode 130 embodiment at the correct angle for x-ray emission 110. Further, the anode 130 embodiment (e.g., disk) can rotate so the points where the electron beams 123 hit can trace out line segments that can distribute the energy over a larger surface area of the anode 130 to reduce damage (e.g., overheating, melting).

Certain exemplary embodiments shown in the figures also illustrate a central x-ray source 120s with a more traditional collimator 112. This central x-ray source(s) 120s can be used to capture traditional x-ray images. Further, the central x-ray source 120s can also be used as one of the distributed sources to capture the multiple projections x-ray images that can be processed to obtain a limited angle tomosynthesis dataset (e.g., by applying reconstruction processing to that data). In one embodiment, the central x-ray source 120s can also use an anode 125 (e.g., separate additional anode) that can move to reduce heating.

Although an exemplary circular arrangement of distributed low power x-ray sources 120, 220 are shown here, other linear or non-linear arrangements or even prescribed patterns (e.g., shapes, stars, diamonds, regular or irregular combinations, repeating) can be used with corresponding selectable array of collimation windows 222 that can provide combined tomosynthesis and projection x-ray imaging. In one embodiment, a plurality of unit arrays (e.g., 6-8 unit arrays) can be implemented as individual straight lines sources, but configured to approximate a circle.

Figure 7:
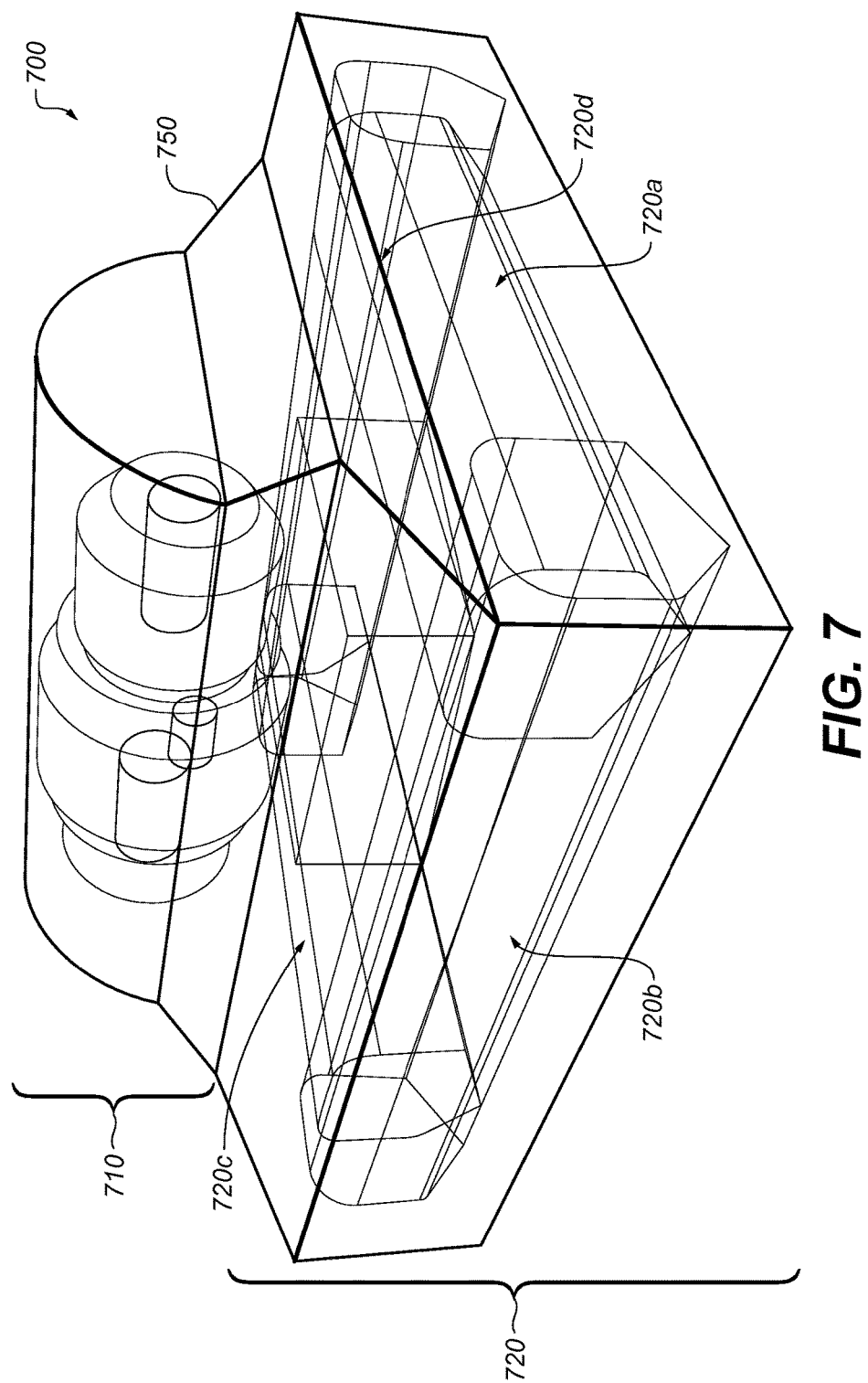
FIG. 7 is a diagram that shows an embodiment of a radiation shield enclosing a combined tomosynthesis and gen rad x-ray source according to embodiments of the application.

In one exemplary embodiment, a standard radiation x-ray source 120s (or at least one distributed source with standard radiation capabilities) can be enclosed in a single radiation shield with a plurality of distributed sources. For example, a carbon-nanotube (CNT) array tube can be packaged along with a traditional tube in the same housing. In one configuration, a single radiation shield enclosing the combination of sources can provide exterior access to the standard radiation x-ray source without disturbing the additional plurality of low power distributed sources. FIG. 7 is a diagram that shows an embodiment of a radiation shield enclosing a combined tomosynthesis and gen rad (e.g., projection x-ray imaging) x-ray source (e.g., x-ray source assembly).

As shown in FIG. 7, a radiation source assembly 700 for radiographic imaging systems and/or methods can implement both projection and tomographic imaging according to embodiments of the application. The radiation source assembly 700 can include a gen rad or first x-ray source 710 to output a beam sufficient for standard projection radiography. The radiation source assembly 700 can include a tomosynthesis imaging source 720 that can be a plurality of groups of distributed sources 720a, 720b, 720c, 720d that can have a prescribed shape. As shown in FIG. 7, the tomosynthesis imaging source 720 that can be a plurality of linearly arranged distributed sources 720a, 720b, 720c, 720d that can be configured in a rectangular shape. The radiation source assembly 700 can output x-ray beams to impinge a digital radiographic detector 140. In one embodiment, one or more collimators for the distributed sources 720a, 720b, 720c, 720d can be selectively adjustable between two or more positions. In one exemplary embodiment, the radiation source assembly 700 can include a shared anode for the distributed sources 720a, 720b, 720c, 720d. Further, the embodiment shown in FIG. 7 can use a selectable collimator for the tomosynthesis imaging source and a separate collimator (e.g., fully adjustable) for the gen rad imaging source. Preferably, the standard radiation x-ray source 710 can be enclosed in a single radiation shield 750 with the tomosynthesis imaging source 720 (e.g., groups of distributed sources 720a, 720b, 720c, 720d). In one embodiment, access can be provided through the single radiation shield 750 to the standard radiation x-ray source 710 without impacting a portion of the radiation shield 750 for the tomosynthesis imaging source 720. In one embodiment, access can be provided through the single radiation shield 750 to the tomosynthesis imaging source 720 (e.g., 720a) without impacting a portion of the radiation shield 750 for the standard radiation x-ray source 710. In one embodiment, the groups of distributed sources 720a, 720b, 720c, 720d can be independently adjusted or have different relative positions relative to a detector upon which corresponding beam shaped emissions will impinge.

In one embodiment, a single radiographic source assembly can allow for the use of a collimated light source corresponding to one source (e.g., gen rad or distributed tomography source) to provide visible guidance for an operator positioning a subject to be exposed by another source (e.g., distributed tomography source or gen rad) of the single radiographic source assembly.

In one embodiment, a single radiographic source assembly can allow for the use of a first generator for each of the gen rad source and a second generator for the tomographic imaging source. In one embodiment, a single radiographic source assembly can allow for the use of a single generator for each of the gen rad source and the tomographic imaging source. In one embodiment, a single radiographic source assembly can allow for the use of a single generator with a single common cable to an anode of the imaging sources.

In one embodiment, a single radiographic source can provide both tomosynthesis and gen rad (e.g., projection) x-ray imaging. For certain exemplary embodiments, the single radiographic source comprises at least two collimators. For example, the at least two collimators can include a first collimator for the gen rad source that is fully adjustable (e.g., 3D x-ray beam shaping) and a second collimator for tomosynthesis imaging that can used limited beam shaping capability (e.g., two directions, two distances or two apertures). A tomosynthesis imaging source can be an array of distributed sources such as a line or ordered sequence (e.g., linear or non-linear) of low power sources (e.g., CNT x-ray sources). In one embodiment, the second collimator can be a tube around the tomosynthesis imaging source that can arrange (e.g., rotate, slide) at least two apertures into place for beam shaping. In another embodiment, the second collimator can be a corresponding unit that can move such as in or out (with one or more apertures) relative to the tomosynthesis imaging source for beam shaping. In another embodiment, the second collimator can be a corresponding unit that can removably attach (e.g., snap in, twist in, hingeably or twist fastener) to the single source at a plurality of positions or locations for tomosynthesis imaging source beam shaping. In one embodiment, the first and second collimators can be discrete adjustable units. In one embodiment, the first and second collimators can be a combined unit. In one embodiment, both the first and second collimators can be within a single radiation shield. Alternatively, one of the first and second collimators can be within the single radiation shield and the other collimator can be outside.

Two different types of x-ray sources including (i) general radiation (gen rad) source and (ii) distributed array of certain number of sources (e.g., lower power) can be included in a single x-ray source for a radiographic imaging system according to embodiments of the application.

One exemplary embodiment for the distributed array of sources can be a configuration that can include 3-20 distributed sources in a unit (e.g., unit array of distributed sources) at sides (e.g., each of 3-8 sides around a central area) to make an arrangement, which configuration can be separated and individually attached by unit array (or fastened together in a single entity) to a mechanical housing (e.g., tube head) of exemplary imaging systems. For certain exemplary embodiments, the unit arrays are not co-planar and can implement a different SID for an imaging event or examination. For example, the unit arrays can be selectively co-planar, for example, two sides at different depths, three of four sides at different planes. Further, the (vertical, horizontal) distance between the unit arrays can be the same or different (e.g., increasing). Alternatively, adjacent or opposite pairs of unit arrays can have equal SIDs or be co-planar. Such a variation in arrangement can allow for a fixed x-ray source arrangement to implement a greater range of subject distances.

By implementing a distributed source in several smaller pieces, certain exemplary embodiments can include independent movement of the plurality of unit arrays of distributed sources. For example, one exemplary embodiment can include a configuration that can make the unit arrays (e.g., four arms) independently adjustable or able to move separately. Thus, individual unit arrays or opposite unit arrays can move outward to provide a wider angular coverage to improve in plane or out of plane resolutions. In one embodiment, such outward movement of at least one unit array can be accompanied by additional adjustment of the unit array to maintain or achieve a desired arrangement or overlapping of x-ray beams from the unit arrays at a DR detector. For example, individual unit arrays can rotate independently (e.g., two opposing edges can rotate outward for an increased SID) to adjust for different SIDs (e.g., increased or decreased) to bring into overlapping on the detector (e.g., focus). In other words, such movement can be included with collimation adjustments by rotating a collimation aperture or switching between a plurality of collimation apertures. However, such rotation can compensate for change in x-ray beam in one dimension (e.g., X-direction or the Y-direction) as the SID changes. In one embodiment, an additional collimation (e.g., third collimation or beam shaping) can be used at a distance closer (e.g., 6 inches-2 feet) to the detector, for example, to provide an outer limitation to the collimated beams of the distributed array of sources.

Certain exemplary embodiments can include independent movement of the plurality of unit arrays of distributed sources to implement different examinations or SIDs. For example, a chest x-ray examination can use a longer SID than a head x-ray examination and accordingly, movement (e.g., spatial positioning and/or rotation) of the unit arrays can allows multiple distances or SIDs to be implemented with a single aperture (e.g., fixed collimation, pinhole) for each distributed source.

Certain exemplary embodiments can include independent movement of the plurality of unit arrays of distributed sources to implement different formations on a mobile x-ray imaging cart or a portable x-ray imaging system. Thus, independent movement of the plurality of unit arrays can use an extended formation of unit arrays that can have a significant length (e.g., 3-8 feet) in an imaging configuration for a mobile x-ray cart that can fold or dis-assemble into a reduced size or 3D footprint to allow the mobile x-ray cart to fit into small areas and though doorways.

In one embodiment, the unit arrays can be attached, adjusted and/or removed without tools. In one embodiment, the unit arrays can be attached and/or rotated between two positions where a first position is outside an area traversed by a central x-ray beam (e.g., gen rad beam) and a second position to cross or cover the area traversed by the central x-ray beam. The second position in such a configuration can reduce an angular disbursement of beams from the distributed array of sources.

In one embodiment, a plurality of unit arrays (e.g., 6-8 unit arrays) can be implemented to move between a small retracted configuration and unfold multiple times to form a prescribed linear or non-linear configuration (e.g., multiple straight lines of sources or unit arrays), which can extend in multiple directions from/around a central beam.

Exemplary system and/or method embodiments according to the application can be used for in-room radiographic imaging systems and/or portable tomosynthesis. Portable tomosynthesis imaging may be able to provide the sought after information at the bedside without subjecting the patient to the risks of transport to radiology. For example, tomosynthesis imaging can supply the required information to diagnose patient conditions that are non-differentiable with standard projection x-ray imaging such as chest x-rays (e.g., without moving the patient).

Consistent with at least one embodiment, exemplary methods can use a computer program with stored instructions that perform on image data that is accessed from an electronic memory. As can be appreciated by those skilled in the image processing arts, a computer program of an embodiment of the application can be utilized by a suitable, general-purpose computer system, such as a personal computer or workstation. However, many other types of computer systems can be used to execute the computer program of the present invention, including an arrangement of networked processors, for example. A computer program for performing exemplary methods according to the application may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing exemplary methods according to the application may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that computer program products of this application may make use of various image manipulation algorithms and processes that are well known. It will be further understood that exemplary computer program product embodiments herein may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or cooperating with the computer program product of the present invention, are not specifically shown or described herein and may be selected from such algorithms, systems, hardware, components and elements known in the art.

As described herein, x-ray sources can use one or more collimators to form beams that are directed through a subject toward a detector. The x-ray sources may also include positioning, such as motors, which allow for directing beams towards the detector. The radiographic imaging system can include at least one display/console and x-ray sources can be coupled thereto. A system controller or control unit can coordinate operations of x-ray sources, detectors (e.g., wirelessly or tethered), and additional radiographic imaging system components. The system controller can control operations of x-ray source or x-ray source assembly, which may include the collimator, positioning devices and triggering of image acquisition by emission of x-rays. The system controller also can control operations of the detector, which may include triggering of the image acquisition and transmission of the acquired images back to the controller. In addition, the system controller can control the movement of a movable transport frame for a mobile radiographic imaging system.

Exemplary functions described herein and/or performed by the diagrams of FIGS. 1-7, the system processor or the radiographic imaging system/unit may be implemented, for example, but not limited to using one or more of a conventional general purpose processor, digital computer, microprocessor, microcontroller, RISC (reduced instruction set computer) processor, CISC (complex instruction set computer) processor, SIMD (single instruction multiple data) processor, signal processor, central processing unit (CPU), arithmetic logic unit (ALU), GPU, video digital signal processor (VDSP) and/or similar computational machines, programmed according to the teachings of the present specification, as will be apparent to those skilled in the relevant art(s). Appropriate software, firmware, coding, routines, instructions, opcodes, microcode, and/or program modules may readily be prepared by skilled programmers based on the teachings of the present disclosure, as will also be apparent to those skilled in the relevant art(s). The software is generally executed from a medium or several media by one or more of the processors of the machine implementation.

Exemplary embodiments according to the application can include various features described herein (individually or in combination).

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Priority is claimed from commonly assigned, copending U.S. Provisional Patent Application Ser. No. 61/755,488 filed Jan. 23, 2013 in the name of Michael D. Heath et al., titled DIRECTED X-RAY FIELDS FOR TOMOSYNTHESIS, the contents of which are incorporated fully herein by reference.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A radiographic imaging system for tomosynthesis x-ray imaging and general projection radiography x-ray imaging, the radiographic imaging system comprising:
   an x-ray source assembly comprising:
   a plurality of distributed x-ray sources in a ring formation, the distributed x-ray sources supported by a ring shaped structure, each of the distributed x-ray sources operable at a first power level for said tomosynthesis x-ray imaging; and a central x-ray source at or near a the central axis of the ring shaped structure, the central x-ray source supported by a central support structure and operable at a second power level greater than the first power level for said general projection radiography x-ray imaging;

an x-ray generator;

a control unit connected to the x-ray generator to control activation of the distributed x-ray sources and the central x-ray source; and a collimator formed in a shape of a ring and comprising a first plurality of openings through the ring, the first plurality of openings each configured to provide fixed collimation for one of the plurality of distributed x-ray sources.

2. The radiographic imaging system of claim 1, wherein the collimator is configured to collimate x-ray beams from the distributed x-ray sources such that the collimated x-ray beams overlap at a first distance from the distributed x-ray sources.

3. The radiographic imaging system of claim 1, wherein the distributed x-ray sources are housed in the same vacuum chamber or in the same radiation shielding.

4. The radiographic imaging system of claim 1, further comprising:

a moveable transport frame; and an adjustable support structure coupled to the moveable transport frame;

wherein the x-ray source assembly is mounted to the adjustable support structure and is configured to direct x-ray radiation towards a subject from the distributed x-ray sources and/or the central x-ray source.

5. A radiographic imaging system for tomosynthesis x-ray imaging and projection x-ray imaging, the radiographic imaging system including:

a first x-ray source;

a first collimator to collimate the first x-ray source, the first collimator configured to be adjustable in at least two transverse dimensions;

a plurality of distributed x-ray sources;

a ring shaped structure configured to support the plurality of distributed x-ray sources in a ring formation, wherein the first x-ray source is at or near a central axis of the ring shaped structure; and a second collimator formed in a shape of a ring, the second collimator comprising a plurality of openings each configured to collimate one of the plurality of distributed x-ray sources.

6. The radiographic imaging system of claim 5, wherein each of the plurality of distributed x-ray sources is configured to output x-rays at a first power level sufficient for tomosynthesis imaging, the first x-ray source is configured to output x-rays at a second power level sufficient for standard projection radiography, and wherein the first power level is less than the second power level.

7. The radiographic imaging system of claim 5, wherein the first x-ray source comprises a radiation shield or a vacuum chamber.

8. The radiographic imaging system of claim 6, further comprising a first generator connected to the first x-ray source and a second generator connected to the plurality of distributed x-ray sources.

9. The radiographic imaging system of claim 5, wherein the second collimator comprises at least four openings each movable between first and second positions to provide different focal lengths for at least two of the distributed x-ray sources.

10. The radiographic imaging system of claim 5, further comprising:

a moveable transport frame;

an adjustable support structure coupled to the moveable transport frame; and control circuitry in the moveable transport frame and coupled to the plurality of distributed x-ray sources, the control circuitry configured to receive projection images each corresponding to one of the plurality of distributed x-ray sources for reconstruction of a tomosynthesis image, wherein the plurality of distributed x-ray sources is mounted to the adjustable support structure.

11. The system of claim 2, wherein the collimator comprises a second plurality of openings each configured to collimate one of the distributed x-ray sources such that the x-ray beams collimated by the second plurality of openings overlap at a second distance from the distributed x-ray sources.

12. The system of claim 2, wherein the collimated x-ray beams overlap within an area of a radiographic detector positioned at the first distance from the distributed x-ray sources.

13. The system of claim 11, wherein the x-ray beams collimated by the second plurality of openings overlap within an area of a radiographic detector positioned at the second distance from the distributed x-ray sources.

14. The system of claim 5, wherein the plurality of openings each comprises a fixed shape opening.

15. The radiographic imaging system of claim 1, wherein the collimator is configured to slide or rotate between a first fixed focal length position and a second fixed focal length position to provide different focal lengths for the plurality of distributed x-ray sources.

16. The radiographic imaging system of claim 5, wherein the second collimator is configured to slide or rotate between a first fixed focal length position and a second fixed focal length position to provide different focal lengths for the plurality of distributed x-ray sources.

* * * * *